United States Patent
Faber et al.

(10) Patent No.: US 7,194,122 B2
(45) Date of Patent: Mar. 20, 2007

(54) MEDICAL TOMOGRAPHY APPARATUS FOR GENERATING A 2D IMAGE FROM A 3D DATASET OF A TOMOGRAPHIC DATA

(75) Inventors: Roland Faber, Uttenreuth (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 676 days.

(21) Appl. No.: 10/264,331

(22) Filed: Oct. 3, 2002

(65) Prior Publication Data
US 2003/0068075 A1 Apr. 10, 2003

(30) Foreign Application Priority Data
Oct. 8, 2001 (DE) .................................. 101 49 556

(51) Int. Cl.
*G06K 9/00* (2006.01)
*G06K 9/36* (2006.01)
*A61B 6/00* (2006.01)

(52) U.S. Cl. .................... 382/131; 382/285; 378/4; 378/21

(58) Field of Classification Search ............. 382/131, 382/285; 378/4, 21; 345/419
See application file for complete search history.

(56) References Cited

U.S. PATENT DOCUMENTS

| | | | |
|---|---|---|---|
| 4,868,748 A | | 9/1989 | Crawford et al. |
| 4,882,679 A | * | 11/1989 | Tuy et al. .................... 600/425 |
| 5,170,347 A | * | 12/1992 | Tuy et al. .................... 345/419 |
| 5,566,282 A | | 10/1996 | Zuiderveld |
| 5,734,384 A | * | 3/1998 | Yanof et al. ................. 345/424 |
| 5,859,891 A | * | 1/1999 | Hibbard ........................ 378/62 |
| 5,898,793 A | * | 4/1999 | Karron et al. ............... 382/131 |
| 6,243,488 B1 | * | 6/2001 | Penna ........................ 382/154 |
| 6,280,387 B1 | * | 8/2001 | Deforge et al. ............. 600/454 |
| 6,464,642 B1 | * | 10/2002 | Kawagishi .................. 600/454 |
| 6,466,185 B2 | * | 10/2002 | Sullivan et al. ................ 345/6 |
| 2002/0126884 A1 | * | 9/2002 | Gerritsen et al. ........... 382/131 |

FOREIGN PATENT DOCUMENTS

| | | |
|---|---|---|
| EP | 0 318 176 | 2/1996 |
| EP | 0318176 B1 * | 2/1996 |

OTHER PUBLICATIONS

"Multiple Brain Atlas Database and Atlas-Based Neuroimaging System," Nowinski et al, Computer Aided Surgery, vol. 2, (1987) pp. 42-66.

(Continued)

*Primary Examiner*—Bhavesh M. Mehta
*Assistant Examiner*—Utpal Shah
(74) *Attorney, Agent, or Firm*—Schiff Hardin LLP

(57) ABSTRACT

A medical tomography apparatus and method, a 3D dataset is generated in as picture elements arranged in a three-dimensional grid during the examination of a patient. Pre-defined surfaces are stored in a library and, dependent on the desired examination, one of the predefined surfaces can be selected with an input unit and thus the shape of an evaluation surface can be defined. Picture elements of the 3D dataset along the evaluation surface and used for constructing a two-dimensional image. A pre-defined surface is selected from the library and is employed for determining the shape of the evaluation surface. The method and the apparatus can be particularly employed in a simple way for the multi-planar reconstruction of a two-dimensional image along a multiply or arbitrarily curved surface.

20 Claims, 2 Drawing Sheets

OTHER PUBLICATIONS

"Specification, Modeling and Visualization of Arbitrarily Shaped Cut Surfaces in the Volume Model," Pflesser et al, Medical Image and Computer-Assisted Intervention, Proc. MICCAI '98 (1998), pp. 853-860.

"Medical Imaging: Digitale Bildanalyze und-kommunikation in der Medizin," Ehricke (1997) p. 87.

* cited by examiner

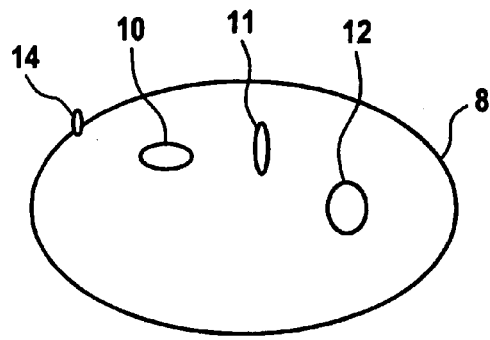
"3D"   FIG 1
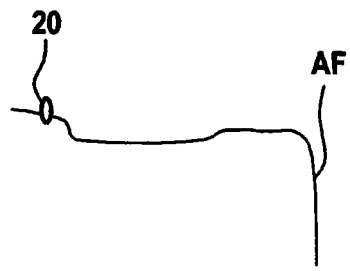
FIG 2
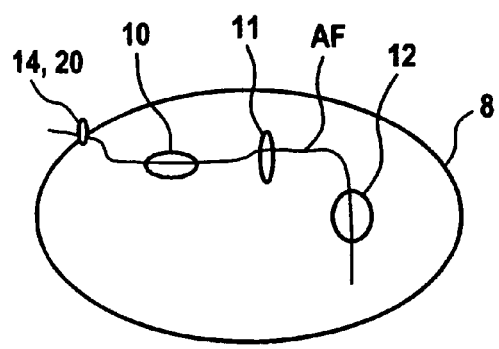
"3D"   FIG 3
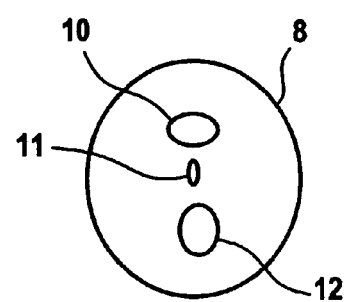
"2D"   FIG 4

MEDICAL TOMOGRAPHY APPARATUS FOR GENERATING A 2D IMAGE FROM A 3D DATASET OF A TOMOGRAPHIC DATA

BACKGROUND OF THE INVENTION

1. Field of the Invention

The present invention is directed to a method for generating a two-dimensional image from a 3D dataset of a tomography apparatus for the medical examination of a patient, wherein the 3D dataset contains picture elements arranged is three-dimensional grid, and wherein an evaluation surface proceeding through the grid is defined and the picture elements along the evaluation surface are employed for constructing the two-dimensional image. The invention is also directed to a medical tomography apparatus with which a 3D dataset is generated in as picture elements in a three-dimensional grid during the examination of a patient, having an input unit for defining an evaluation surface proceeding through the grid, and having an evaluation unit for constructing a two-dimensional image from the 3D dataset using the picture elements along the evaluation surface. The invention is also directed to a data carrier for such a method.

2. Description of the Prior Art

Spatial tomogram sequences with isotropic resolution, i.e. with the same spatial resolution in the x, y and z direction, or with approximately isotropic resolution can be generated with medical tomographic image acquisition methods. Such image acquisition methods are involved, for example, in computed tomography (spiral CT), in three-dimensional magnetic resonance tomography, and in 3D ultrasound examinations. The tomogram sequences respectively arising in the acquisition are referred to as volume data. They can be interpreted as a three-dimensional, regular grid, wherein tissue properties at every intersecting point are represented by a gray scale values. Alternatively, the volume data can be imaged as a large cuboid composed exclusively of identical cuboids. An elementary cuboid is called a voxel, has a gray scale value, and covers a certain tissue volume. Volume data, i.e. 3D datasets, also can be generated by conventional x-ray devices, for example by a C-arm device.

Two-dimensional images must be acquired for visualizing the volume data, i.e. the 3D dataset, for the viewer, for example a physician. The presentation of the original tomograms often has little diagnostic utility or do not allow certain viewing modes at all. For visualization, it is known to generate presentations referred to as pseudo-3D presentations (three-dimensional visualizations). An example is the method of maximum projection (maximum intensity projection) that is particularly significant for angiography. In this method, the highest intensity value of the gray scale values encountered on a projection beam is selected and imaged into the observer image plane. In the maximum projection, the entire volume is imaged and can be viewed in every direction. Maximum projection is disclosed, for example, by U.S. Pat. No. 5,566,282.

The visualization of the volume data also is possible by means of reconstruction of secondary slices through the data grid. Such a method is the known multi-planar reconstruction. Arbitrarily oriented tomograms are calculated through the data volume. The method is of significance particularly for computed tomography because only tomograms in the transverse direction—or in a direction deviating slightly therefrom given a tiltable gantry—can be generated as original slices, i.e. as primary images. For example, longitudinal sections can be generated from the 3D dataset with multi-planar reconstruction. In multi-planar reconstruction, interpolation is carried out between grid points or voxels for generating a two-dimensional image, for example according to the method of the nearest neighbor interpolation or the method of tri-linear interpolation.

U.S. Pat. Nos. 5,898,793, 4,868,748 and 4,821,213 disclose methods with which boundary surfaces within a 3D dataset can be presented, for example bone and/or tissue boundary surfaces. The boundary surfaces first must be characterized or defined by the operating personnel by means of a limit value or an interval for their density value before a mathematical method then allows a decision to be made as to the affiliation of a particular voxel to a boundary surface, or to a number of boundary surfaces.

The text by Hans-Heino Ehricke, "Medical Imaging: Digitale Bildanalyse und-kommunikation in der Medizin", Vieweg, 1997, page 87, discloses that planes be defined, and reconstructed from the data volume, and presented as image on the operating console of the image acquisition device or at a separate image workstation for interactive reconstruction of secondary slices. The planes are oriented orthogonally relative to the grid axes, slanting or doubly slanting planes, or completely arbitrarily curved sections. As a result, the structures of interest (for example, optical nerve, spinal column) that are distributed over many images in the original sections can be presented in a single tomogram.

Multi-planar reconstruction is particularly tedious for medical personnel when a secondary section, i.e. an evaluation surface proceeding through the grid, must be defined with high complexity. For example, it is tedious to define or determine a curved evaluation surface in a number of dimensions. Methods that require an input of a parameter (for example, density value) of a specific surface are susceptible to error and/or require experience, or trial and error.

SUMMARY OF THE INVENTION

It is an object of the present invention to provide a medical tomography apparatus and method for generating a 2D image from 3D dataset of tomographic data wherein the above-noted disadvantages of known methods and systems are avoided, or at least minimized.

The above object is inventively achieved in a method of the initially-described type wherein a pre-defined surface is selected from a library and is employed for defining the shape of the evaluation surface.

For example, the library is stored in an electronic or magnetic storage device.

A tomography apparatus of implementing the method of the invention can be, for example, a magnetic resonance apparatus, a computed tomography apparatus or an x-ray device that generates 3D data.

Preferably, the pre-defined surface is selected dependent on a desired radiological interpretation and/or question or a surface adapted to a structure to be examined or to a region of the patient to be examined is selected as the pre-defined surface.

The method of the invention achieves the advantage that an evaluation surface, particularly a complex evaluation surface, need only be generated once in advance as pre-defined surface and—after it has been stored in this way in the library—can be employed repeatedly without having to implement the surface definition anew.

Radiological questions to which the pre-defined surfaces are adapted are, for example, examinations of the external shape of the heart as a whole, examinations of the heart in parts, for example for presentation of the coronary artery, examinations of the knee directed to the joint surfaces, or examinations at the knee having cross-sectional presentations through the meniscus, etc.

It is an advantage of the invention that radiological questions as derived from presentations in pathological textbooks and reference books can be directly replicated. Such books often show curved surfaces in a plane projection in order to make the relevant information optimally accessible to the eye of the observer. Structures of the patient to which pre-defined surfaces can be adapted are, for example, the spinal column, structures of the knee joint, the course of specific blood vessels (carotid artery, aorta), the course of specific nerves (spinal channel), etc.

In particular, a surface curved in multiple dimensions is selected as predefined surface. The surface thus can have an arbitrary curvature.

In a preferred embodiment, the evaluation surface is defined by scaling the pre-defined surface with a measured quantity of the patient. As a result thereof, it becomes possible to store the pre-defined surfaces as quasi-standardized surfaces in the library that merely reproduce the shape of the evaluation surface. Only a comparatively small number of surfaces thus need to be stored. The measured quantity of the patient that is employed can either be separately measured or can be a measured quantity that can likewise be obtained by measurement using the tomography apparatus, for example the head diameter of the patient.

In an embodiment of the method, a digital marking attached to the predefined surface and that corresponds to a characteristic structure feature of the patient is aligned at the structure feature visible in the 3D dataset for the correct positioning of the evaluation surface. The alignment occurs either interactively by the operator or automatically via an image analysis process, for example with "mutual information".

The above object also is achieved in accordance with the invention medical tomography apparatus with a library having predefined surfaces for defining the shape of the evaluation surface, with one of the predefined surfaces being selectable via an input unit.

The advantages, embodiments and developments described above for the method apply analogously to the tomography apparatus of the invention.

Preferably, the library contains predefined surfaces for different radiological interpretations and/or questions.

The library likewise preferably contains predefined surfaces for different structures or regions of the patient to be examined.

In a preferred development, the tomography apparatus has a scaling unit for defining the evaluation surface by scaling the predefined surface with a measured quantity of the patient.

In another embodiment, the predefined surfaces of the library have respective digital markings that correspond to a characteristic structure feature of the patient.

For correct positioning of the evaluation surface, a display unit is provided for the simultaneous display of the 3D dataset and the digital marking, so that an alignment of the digital marking of the selected, predefined surface to the characteristic structure feature of the patient visible in the 3D dataset can be interactively performed by the user in a simple way.

A data carrier of the invention contains a library of predefined surfaces for defining the shape of an evaluation surface for the method of the invention.

The library preferably contains predefined surfaces for different radiological evaluations and/or questions or predefined surfaces for different structures or regions of the patient to be examined.

In an embodiment, the predefined surfaces contain respective digital markings that correspond to a characteristic structure feature of the patient.

DESCRIPTION OF THE DRAWINGS

FIG. 1 is a schematic illustration of a real anatomy as registered in a 3D dataset for use in the inventive method and apparatus.

FIG. 2 illustrates an evaluation surface acquired from a predefined surface for use in the inventive method and apparatus, shown schematically.

FIG. 3 is a superimposition of FIGS. 1 and 2.

FIG. 4 schematically illustrates a two-dimensional image acquired according to the method of the invention.

DESCRIPTION OF THE PREFERRED EMBODIMENTS

Figure 5:
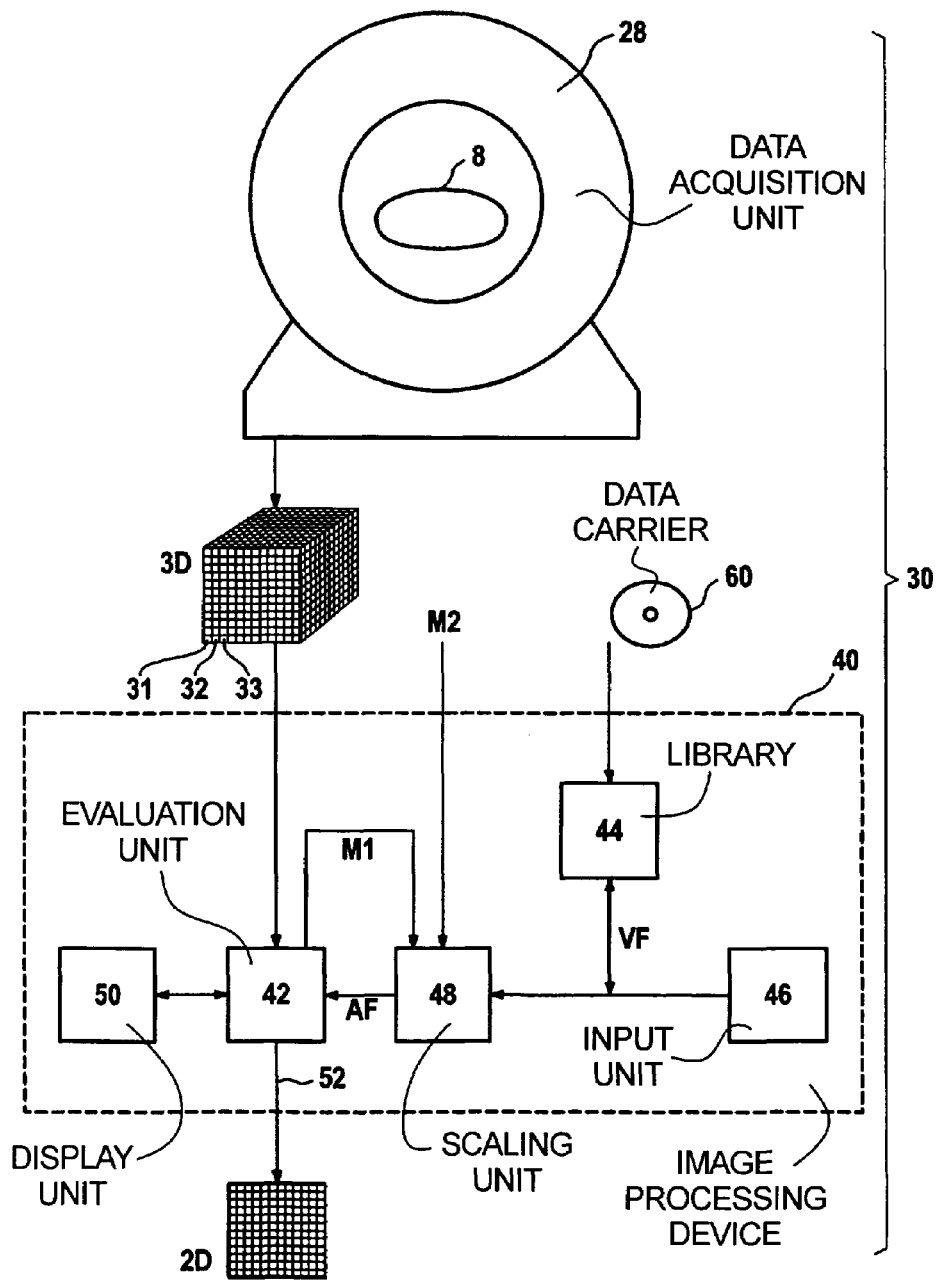
FIG. 5 schematically illustrates a medical tomography apparatus of the invention.

FIG. 1 shows a real anatomy of a patient 8 acquired in a 3D dataset 3D with structures 10, 11, 12 shown as examples, such as nerves, blood vessels, bones, etc. An emphasized, characteristic or easily identifiable structure feature 14 is likewise shown.

It is clear that the 3D dataset 3D has been shown only two-dimensionally in FIG. 1 (as well as in FIG. 3).

FIG. 2 indicates an evaluation surface AF that was acquired from a previously generated, predefined surface VF (see FIG. 5) that was stored in a library 44 (see FIG. 5). Just like the predefined surface VF, the evaluation surface AF contains a digital marking 20 that corresponds to the characteristic structure feature 14, for example a bone part that can be especially easily recognized.

The logical anatomical landmark or the digital marking 20 is brought into coincidence in FIG. 3 with the anatomical landmark or the structure feature 14 of the patient 8. For correct alignment and positioning of the evaluation surface AF, a number of structure feature 14 and digital markings 20 also can be present. Bringing the digital marking 20 into coincidence with the structure feature 18 occurs either interactively by the user or automatically via an image analysis process with pattern recognition.

The picture elements in the 3D dataset 3D along the multiply curved evaluation surface AF are employed for the construction of the two-dimensional image 2D, as schematically shown in FIG. 4. Interpolation is thereby carried out between grid points or voxels.

The two-dimensional image 2D shown in FIG. 4 is not a real two-dimensional image; but serves to make complex structures accessible to the observer.

It is not necessary for the observer to manually define a new evaluation surface AF repeatedly in a time-consuming way, this evaluation surface AF possibly being multiply curved. Instead, the time expenditure is advantageously reduced to the minimum of adapting a predefined surface VF or multiplicity to the specific anatomical conditions.

FIG. 5 shows a tomography apparatus 30 that is suitable for the implementation of the method. It has a data acquisition unit 28 operating, for example, according to computed tomography or magnetic resonance tomography principles, comprises an image processing device 40. The data acquisition unit 28 generates a 3D dataset 3D of the patient 8 with voxels or picture elements 31, 32, 33, . . . , that in a three-dimensional grid represent an examined region of the patient 8. The 3D dataset 3D has arisen, for example, by stacking individual tomograms on top of one another.

The 3D dataset 3D is supplied via a data line to an evaluation unit 42 of the image processing device 40. The evaluation unit 42 is in communication via data lines to a library 44 fashioned, for example, as a data memory of a computer wherein predefined surfaces VF are stored. A user can select one of the predefined surfaces VF via an input unit 46, for example dependent on a desired radiological evaluation or question or dependent on a specific structure of the patient 8 to be examined.

After the selection has been carried out, the predefined surface VF is supplied to a scaling unit 48 wherein the predefined surface VF is adapted by linear multiplication by a measured quantity M1, M2 to the specific body size of the patient 8 currently under examination. The measured quantity Ml either can be calculated from the measurement of the pickup unit 28 by the evaluation unit 42 or, on the other hand, the measured quantity M2 is manually entered by the user. For example, the measured quantity M1, M2 is the head diameter or the length of an extremity of the patient 8.

Only the shape, i.e. particularly the gradients and curvatures, of the evaluation surface AF respectively needed for the examination of a specific patient is stored in the predefined surface VF. The adaptation of the predefined surfaces VF to the specific size of the patient 8 occurs in the scaling unit 48.

The evaluation unit 42 presents the 3D dataset 3D—at least excerpts thereof—together with the evaluation surface AF generated by the scaling unit 48 on a display unit 50 configured as picture screen, so that the user can bring the digital marking 20 (shown in FIG. 2) into coincidence with the particular structure feature 14 via the input unit 46 (matching).

After the matching of the evaluation surface AF with the 3D dataset 3D, the evaluation unit 42 calculates a two-dimensional image 2D by interpolation between data points along the evaluation surface AF. The known methods of multi-planar reconstruction can be used for this purpose. The two-dimensional image 2D generated in this way is available at an output line 52 and/or can be presented on a picture screen.

The image processing device 40 together with its described components is implemented, for example, as a computer. Accordingly, the library can be realized by a drive, for example by a floppy drive or a CD-ROM drive in which a data carrier 60 is loaded, the library with the predefined surfaces VF being stored on said data carrier 60. The predefined surfaces VF on the data carrier 60 are generated before the actual examination of the patient 8 and are always available to the medical personnel at the tomography apparatus 30 without having to be generated anew each time with high time expenditure.

Although modifications and changes may be suggested by those skilled in the art, it is the intention of the inventors to embody within the patent warranted hereon all changes and modifications as reasonably and properly come within the scope of their contribution to the art.

We claim:

1. A method for generating a two-dimensional image from a three-dimensional dataset of tomography data obtained in a medical examination of a patient, said three-dimensional dataset containing picture elements arranged in a three-dimensional grid, comprising the steps of:

in a computer, defining a two-dimensional evaluation surface proceeding through said three-dimensional grid and employing only picture elements along said two dimensional evaluation surface for constructing a two-dimensional image;

storing a plurality of predefined two dimensional surfaces in a library accessible by said computer; and selecting one of said predefined surfaces from said library for defining a shape of said two dimensional evaluation surface.

2. A method as claimed in claim 1 comprising selecting said one of said surfaces from said library dependent on a radiological interpretation to be implemented.

3. A method as claimed in claim 1 comprising selecting said one of said surfaces from said library dependent on a radiological question to be answered.

4. A method as claimed in claim 1 comprising selecting said one of said surfaces as a surface adapted to a portion of said patient, selected from the group consisting of an anatomical structure of said patient and a region of said patient.

5. A method as claimed in claim 1 comprising selecting said one of said surfaces from said library as a surface that is curved in a plurality of dimensions.

6. A method as claimed in claim 1 comprising defining said evaluation surface by scaling said one of said surfaces selected from said library with a measured quantity of said patient.

7. A method as claimed in claim 1 wherein said one of said surfaces selected from said library contains a characteristic structural feature of said patient, and comprising the additional step of attaching a digital marking to said one of said surfaces selected from said library for aligning said structural feature in said one of said surfaces to the same structural feature in said three-dimensional dataset for correctly positioning said evaluation surface relative to said three-dimensional dataset.

8. A medical tomography apparatus for generating a two-dimensional image from a three-dimensional dataset of tomography data obtained in a medical examination of a patient, said three-dimensional dataset containing picture elements arranged in a three-dimensional grid, comprising the steps of a computer which defines a two dimensional evaluation surface proceeding through said grid and employs only picture elements along said evaluation surface for constructing a two-dimensional image;

a library accessible by said computer in which a plurality of predefined two dimensional surfaces are stored; and an interface unit connected to said computer allowing selection of one of said predefined two dimensional surfaces from said library for defining a shape of said two dimensional evaluation surface.

9. A medical tomography apparatus as claimed in claim 8 wherein said interface unit allows selection of said one of said surfaces from said library dependent on a radiological interpretation to be implemented.

10. A medical tomography apparatus as claimed in claim 8 wherein said interface unit allows selection of said one of said surfaces from said library dependent on a radiological question to be answered.

11. A medical tomography apparatus as claimed in claim 8 wherein said interface unit allows selection of said one of said surfaces as a surface adapted to a portion of said patient, selected from the group consisting of an anatomical structure of said patient and a region, of said patient.

12. A medical tomography apparatus as claimed in claim 8 wherein said interface unit allows selection of said one of said surfaces from said library as a surface that is curved in a plurality of dimensions.

13. A medical tomography apparatus as claimed in claim 8 wherein said computer defines said evaluation surface by scaling said one of said surfaces selected from said library with a measured quantity of said patient.

14. A medical tomography apparatus as claimed in claim 8 wherein at least one of said surfaces stored in said library contains a characteristic structural feature of said patient, and wherein said at least one of said surfaces is stored in said library with a digital marking attached thereto for aligning said structural feature in said one of said surfaces to the same structural feature in said three-dimensional dataset for correctly positioning said evaluation surface relative to said three-dimensional dataset.

15. A computer-readable medium encoded with a stat structure, loadable into a computer for generating a two-dimensional image from a three-dimensional dataset of tomography data obtained in a medical examination of a patient, said three-dimensional dataset containing picture elements arranged in a three-dimensional grid, said computer defining a two dimensional evaluation surface proceeding through said grid and employing only picture elements along said two dimensional evaluation surface for constructing a two-dimensional image, said data structure containing:

a library of a plurality of predefined surfaces which when, selected via an interface unit of said computer, respectively define a shape of said two dimensional evaluation surface.

16. A computer-readable medium as claimed in claim 15 containing predefined surfaces for respectively different radiological interpretations.

17. A computer-readable medium as claimed in claim 15 comprising containing predefined surfaces for respectively different radiological questions.

18. A computer-readable medium as claimed in claim 15 containing predefined surfaces adapted to a portion of said patient, selected from the group consisting of an anatomical structure of said patient and a region of said patient.

19. A computer-readable medium as claimed in claim 15 containing predefined surfaces that are curved in a plurality of dimensions.

20. A computer-readable medium as claimed in claim 15 wherein at least one of said surfaces in said library contains a characteristic structural feature of said patient, a digital marking to said at least one of said surfaces for allowing said computer to align said structural feature in said one of said surfaces to the same structural feature in said three-dimensional dataset to correctly position said two dimensional evaluation surface relative to said three-dimensional dataset.

* * * * *